(12) United States Patent
Yoshie et al.

(10) Patent No.: US 6,613,925 B1
(45) Date of Patent: Sep. 2, 2003

(54) PROCESS FOR PRODUCING O-ALKYL-N-CYANOIMIDATE

(75) Inventors: Takehiko Yoshie, Kamiichi-machi (JP); Hidenori Nitta, Fujisawa (JP); Youichi Fukunishi, Uozu (JP)

(73) Assignee: Nippon Carbide Kogyo K.K., Tokyo (JP)

( * ) Notice: Subject to any disclaimer, the term of this patent is extended or adjusted under 35 U.S.C. 154(b) by 0 days.

(21) Appl. No.: 09/786,629

(22) PCT Filed: Sep. 9, 1999

(86) PCT No.: PCT/JP99/04896

§ 371 (c)(1), (2), (4) Date: Mar. 7, 2001

(87) PCT Pub. No.: WO00/14056

PCT Pub. Date: Mar. 16, 2000

(30) Foreign Application Priority Data

Sep. 9, 1998 (JP) ............................................ 10-270499
Sep. 9, 1998 (JP) ............................................ 10-270500

(51) Int. Cl.[7] ............................................ C07C 257/04
(52) U.S. Cl. ............................................ 558/9
(58) Field of Search ............................................ 558/9

(56) References Cited

U.S. PATENT DOCUMENTS 4,477,421 A  10/1984  Weiss ......................... 423/275

FOREIGN PATENT DOCUMENTS

JP  10-059922  3/1998
JP  10130220  *  5/1998

* cited by examiner

Primary Examiner—Alan L. Rotman
Assistant Examiner—Ebenezer Sackey
(74) Attorney, Agent, or Firm—Sherman & Shalloway

(57) ABSTRACT

Here is provided a process of preparing an O-alkyl-N-cyanoacetimidate from cyanamide and an orthoacetic acid ester on an industrial scale and in a high yield using an inexpensive apparatus. In preparing an O-alkyl-N-cyanoacetimidate by reaction of an orthoacetic acid ester with cyanamide, the start of the reaction is made in the presence of an alkaline catalyst.

6 Claims, 1 Drawing Sheet

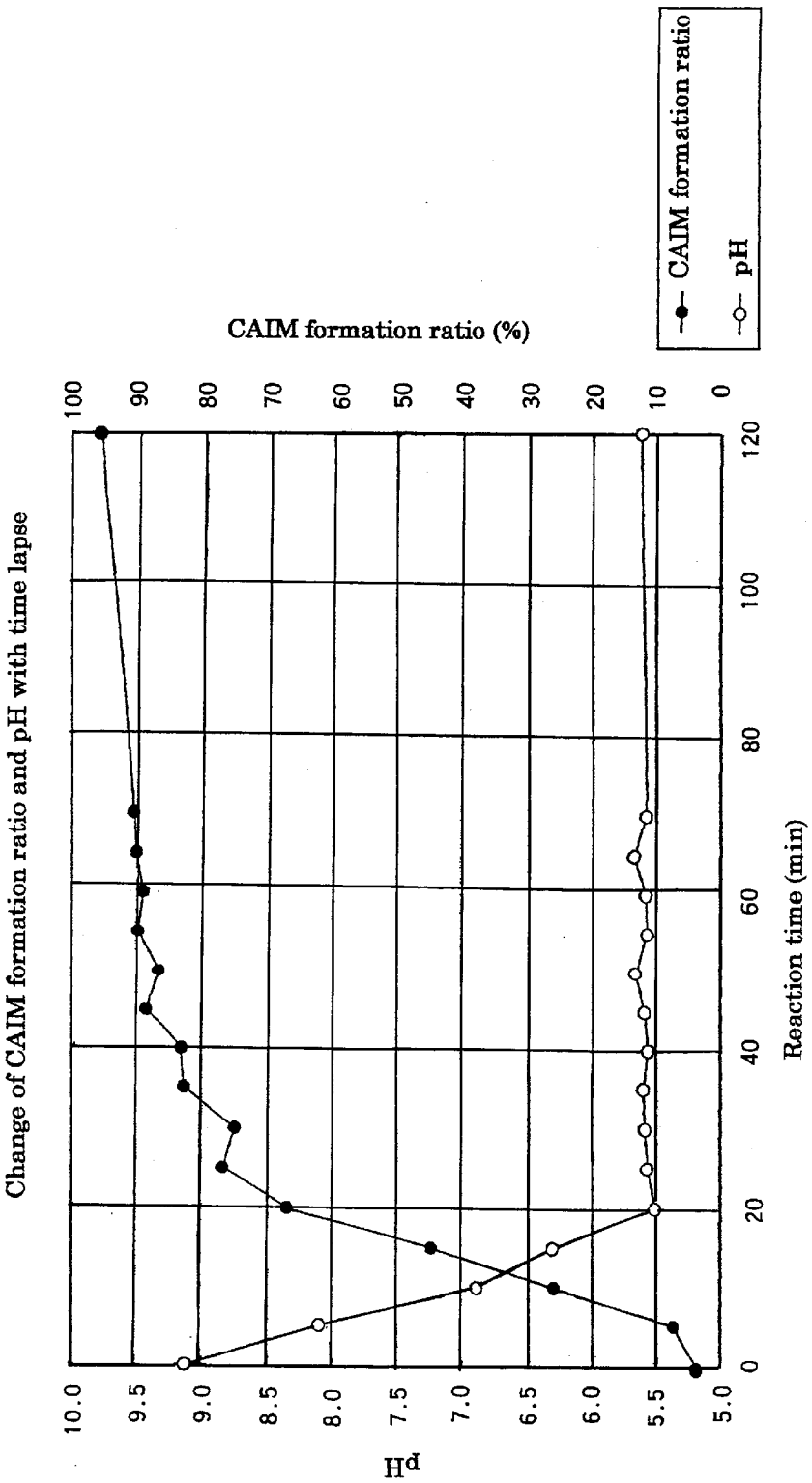

PROCESS FOR PRODUCING O-ALKYL-N-CYANOIMIDATE

TECHNICAL FIELD

This invention relates to a process of preparing an O-alkyl-N-cyanoacetimidate useful as an intermediate of pharmaceuticals and agricultural chemicals. In particular, this invention relates to, in preparing an O-alkyl-N-cyanoacetimidate by reaction of an orthoacetic acid ester with cyanamide, a process of preparing an O-alkyl-N-cyanoacetimidate which comprises making the start of the reaction in the presence of an alkaline catalyst.

BACKGROUND ART

As to a process of preparing an O-alkyl-N-cyanoacetimidate by reaction of an orthoacetic acid ester with cyanamide, some processes have hitherto been known, and for example, Journal of Organic Chemistry, volume 28(1963), page 1816 discloses a process of preparing an O-alkyl-N-cyanoimidate by carrying out the above reaction in the presence of 2 moles of acetic anhydride. In this reaction, as shown in the following reaction equation (1), orthoacetic acid triethyl ester reacts with cyanamide to form O-ethyl-N-cyanoacetimidate and corresponding 2 moles of ethanol, and this ethanol reacts with acetic anhydride to form 2 moles of acetic acid and 2 moles of acetic acid ethyl ester.

Reaction equation (1)

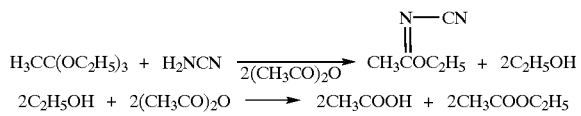

However, this process could not be said to be a suitable process in putting into practice on an industrial scale because separation of the by-products and isolation of the product are difficult.

In U.S. Pat. No. 4,956,503 (DE 3,815,084) is proposed, as shown in the following reaction equation (2), a process of preparing an O-alkyl-N-cyanoacetimidate on an industrial scale by reacting an orthoacetic acid trimethyl ester with cyanamide in an alcoholic solution in the presence of an acidic catalyst.

Reaction equation (2)

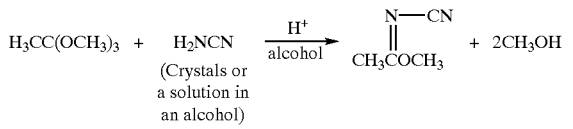

However, although it is proposed in the preparation process that cyanamide is reacted in an alcoholic solution in the presence of an acidic catalyst, the reaction is carried out under an acidic condition, and thus the material of the reaction vessel should be taken into account and there is the possibility that a usual stainless steel reaction vessel corrodes.

The object of the invention lies in providing, in preparing an O-alkyl-N-cyanoacetimidate, a process of preparing an O-alkyl-N-cyanoacetimidate (hereinafter sometimes abbreviated as CAIM) easily and in a high yield on an industrial scale, without selection of a reaction vessel even by use of an inexpensive iron or stainless steel reaction vessel.

DISCLOSURE OF INVENTION

The present inventors have intensely studied for solving the above object, and as a result they found that in preparing an O-alkyl-N-cyanoacetimidate by reaction of an orthoacetic acid ester with cyanamide, the O-alkyl-N-cyanoacetimidate could be prepared easily and in a high yield by making the start of reaction in the presence of an alkaline catalyst, and completed the invention.

BRIEF DESCRIPTION OF DRAWING

FIG. 1 is a drawing showing relations between reaction time and the formation ratio (%) of the O-alkyl-N-cyanoacetimidate (CAIM) and pH in an embodiment of the reaction of the invention.

EMBODIMENTS OF THE INVENTION

The invention is detailedly described below.

Cyanamide contains about 5% or less of water derived from its preparation process. It is very difficult to remove this water.

When an acidic catalyst is used in preparation of CAIM, as shown for example in U.S. Pat. No. 4,956,503 (DE 3,815,984), the problem of corrosion arises due to the presence of water at the time of start of loading or the initial stage of reaction.

However, even when the pH of the reaction system lowers up to about 5, the problem of corrosion does not arise as long as there is no water in the reaction system.

Since in the initial stage of reaction, CAIM itself formed by the reaction is an acidic substance and dissolves in the reaction medium, the pH of the reaction system lowers (see the following reaction equation (3)).

Reaction equation (3)

The orthoacetic acid ester as a main raw material reacts with a small amount of water contained in cyanamide to form 2 moles of methanol and 1 mole of methyl acetate, as shown in the following reaction equation (4). Since by this reason, at a stage when the reaction progressed in some degree, water is consumed by the orthoacetic acid trimethyl ester, the presence of water does not get to be a large problem. Namely, water gives much bad influence at the initial stage of reaction.

Reaction equation (4)

However, when the start of reaction is made in the presence of an alkaline catalyst, for example triethanolamine or triethylamine, the pH can be maintained at for example 8.5 or more (about 5 minutes), as shown in FIG. 1, and in the meanwhile, water can be consumed according to the above reaction equation, and the way is extremely advantageous since it is possible to use an iron or stainless steel reaction vessel (not glass lining).

A highly purified orthoacetic acid ester is used. The pH of a fully purified orthoacetic acid ester is 6.5($1.5 \times 10^{-7}$ per mole of the orthoacetic acid ester). When the reaction progresses under an acidic condition, it is necessary to add a more of the alkaline catalyst. The amount of orthoacetic acid ester used is 0.8 to 2 times, preferably 0.9 to 1.2 times, more preferably 0.95 to 1.04 times the molar amount of cyanamide. However, when water is contained in cyanamide, the orthoacetic acid ester in an amount corresponding to the amount of the water is required.

Cyanamide is used after being dissolved or dispersed in a suitable solvent such as an alcohol. If possible, cyanamide can be reacted as it is as crystals with the orthoacetic acid ester. As to cyanamide, it is desirable to use cyanamide containing as little as water, and the moisture content(water content) is usually 5% or less, preferably 2% or less, particularly preferably is 1% or less based on cyanamide. Further, since cyanamide contains a small amount of an acidic stabilizer such as phosphoric acid, it is necessary to use the alkaline catalyst in an amount corresponding to the phosphoric acid.

The alkaline catalyst does not react with cyanamide, orthoacetic acid esters and alcohols, for example sodium alcoholates such as sodium methylate, amines such as triethanolamine, triethylamine aromatic amines such as pyridine, etc. In view of economical efficiency and easiness of handling, triethanolamine and triethylamine are particularly preferred. Since triethanolamine is distilled off as a distillate in the concentration of the O-alkyl-N-cyanoacetimidate, it is also recyclable.

The use amount of the alkaline catalyst is varied depending also on cyanamide and an orthoacetic acid ester used, but is such an alkali amount that the pH of the reaction mixture at the start of reaction gets to be the range of 7.5 or more, preferably 8.5 to 9.5.

The reaction temperature is 40° C. to 100° C., preferably 60° C. to 80° C. The reaction time is 3 hours to 24 hours, preferably 4 hours to 12 hours. After the reaction, it should be confirmed that cyanamide does not remain in the reaction mixture.

Isolation of the formed O-alkyl-N-cyanoacetimidate is made by distillation, it is recommended to carry out the distillation under such a condition that the temperature inside the vessel does not exceed 100° C., preferably at 60° C. to 80° C., particularly preferably under such a reduced pressure that the temperature of distillates gets to be 50° C. or less. Under such a condition that the temperature inside the vessel does not exceed 100° C., decomposition of the O-alkyl-N-cyanoacetimidate formed in the vessel scarcely occurs.

The invention of the application is further described below according to examples.

EXAMPLE 1

Orthoacetic acid trimethyl ester [63.42 g(0.503 mole); pH 6.5: $4.2 \times 10^{-8}$ per mole of orthoacetic acid trimethyl ester] and 0.04g of triethylamine were added into a 200-ml four-necked flask equipped with a stirring apparatus, a cooling apparatus, distilling receiver and a thermometer (the pH of the mixture was 9.1). Crystalline cyanamide [21.23 g (0.500 mole); moisture content 1.0%; the pH of an aqueous 50% solution is 5.5, $2.7 \times 10^{-7}$ per mole of the orthoacetic acid trimethyl ester] was added thereinto. The pH of the reaction mixture at this time was 8.7(12° C.).

This reaction mixture was heated to react for 6 hours in a reflux state, and thereby 84.1 g of a reaction mixture (the concentration of the O-methyl-N-cyanoacetimidate 57.1%, conversion 97.9%) was obtained. This reaction mixture was vacuum distilled under a condition of 75 to 78° C./10 mmHg to obtain 44.6 g (0.451 mole: yield based on cyanamide 90.2%) of the O-methyl-N-cyanoacetimidate of a purity of 99.2%.

The reaction time (minute) of the reaction, and changes of the pH of the reaction system and the formation ratio of CAIM with time lapse are shown in the attached graph of FIG. 1.

EXAMPLE 2

Reaction was carried out in the same manner as in Example 1 except for change of the alkaline substance for an aqueous 50% caustic soda solution (the pH of the reaction mixture at the time of the addition of cyanamide was 9.3) to obtain 84.2 g (0.480 mole, conversion 95.9%) of a reaction mixture. Distillation was carried out also in the same manner as in Example 1 to obtain 43.7 g (0.441 mole, yield based on cyanamide 88.2%) of the O-methyl-N-cyanoacetimidate of a purity of 99.1%.

EXAMPLE 3

Reaction was carried out in the same manner as in Example 1 except that he reaction time was made to 4 hours to obtain 76.7 g (conversion 89.3%) of a reaction mixture. When this reaction mixture after completion of the reaction was analyzed by gas chromatography, about 0.04% by weight of triethylamine was confirmed.

COMPARATIVE EXAMPLE 1

Reaction was carried out in the same manner as in Example 1 except that the triethylamine of Example 1 and the reaction time changed for 0.05 g of sulfuric acid and 4 hours, respectively, to obtain 78.7 g (conversion 91.6%) of a reaction mixture.

EXAMPLE 4

Orthoacetic acid trimethyl ester [63.26 g (0.5116 mole); pH $8.6=3.0 \times 10^{-10}$ mole of free protons per mole of orthoacetic acid trimethyl ester] and 0.05 g of triethanolamine were added into a 100-ml four-necked flask equipped with a stirring apparatus, a cooling apparatus, a pH meter, a thermometer and a distillation apparatus [the pH of the mixture was 9.1(fee protons per mole of orthoacetic acid trimethyl ester 9.9 $10^{-11}$))]. Crystalline cyanamide [21.23 g (0.5021 mole); moisture content 0.9%; the pH of an aqueous 50% solution was 5.4, free protons per mole of cyanamide was $3.2 \times 10^{-7}$] was added thereinto and dissolved therein [free protons per mole of orthoacetic acid trimethyl ester of the reaction mixture pH 8.7 (12° C.)=$3.5 \times 10^{-10}$].

The reaction mixture was heated, and reaction was carried out at 67° C. for 6 hours while adding triethanolamine so that the pH might not lower to 7 or less to maintain the pH at a range of 7.0 to 8.0 (the total of the addition amount of triethanolamine was 2.8 g), and thereby 86.6 g of a reaction mixture was obtained. When this reaction mixture was analyzed, the purity of the O-methyl-N-cyanoacetimidate was 51.0%(conversion 90.0%).

EXAMPLE 5

Reaction was carried out for 6 hours in the same manner as in Example 4 except that 2.8 g of triethanolamine was added [the pH of the mixture was 9.4(free protons per mole of orthoacetic acid trimethyl ester was $5.0 \times 10^{-11}$mole)] prior to start of the reaction in place of its addition in Example 4 to obtain 87.2 g of a reaction mixture. When this reaction mixture was analyzed, the purity of the O-methyl-N-cyanoacetimidate was 48.8% (conversion 86.8%).

What is claimed is:

1. A process for preparing an O-alkyl-N-cyanoacetimidate which comprises reacting an orthoacetic acid ester with cyanamide which is characterized by making the start of the reaction in the presence of an alkaline catalyst.

2. The process of preparing an O-alkyl-N-cyanoacetimidate according to claim 1 wherein the start of the reaction is made in the presence of an alkaline catalyst and under a condition of pH 7.5 or more.

3. The process for preparing an O-alkyl-N-cyanoacetimidate according to claim 1 wherein the start of the reaction is made in the presence of an alkaline catalyst and under a condition of 8.5 to 9.5.

4. The preparation process according to claim 1 wherein the alkaline catalyst is an aprotic organic amine.

5. The preparation process according claim 2 wherein the alkaline catalyst is an aprotic organic amine.

6. The preparation process according to claim 3 wherein the alkaline catalyst is an aprotic organic amine.

\* \* \* \* \*